(12) United States Patent
Ibrahim et al.

(10) Patent No.: US 8,129,404 B2
(45) Date of Patent: Mar. 6, 2012

(54) COMPOUNDS AND USES THEREOF

(75) Inventors: Prabha N. Ibrahim, Mountain View, CA (US); Wayne Spevak, Berkeley, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 12/721,500

(22) Filed: Mar. 10, 2010

(65) Prior Publication Data

US 2010/0234418 A1 Sep. 16, 2010

Related U.S. Application Data

(60) Provisional application No. 61/159,401, filed on Mar. 11, 2009, provisional application No. 61/159,407, filed on Mar. 11, 2009.

(51) Int. Cl.
| | |
|---|---|
| *C07D 471/02* | (2006.01) |
| *C07D 491/02* | (2006.01) |
| *C07D 498/02* | (2006.01) |
| *A01N 43/42* | (2006.01) |
| *A61K 31/44* | (2006.01) |

(52) U.S. Cl. ....................... 514/300; 546/113
(58) Field of Classification Search ............ 514/300; 546/113
See application file for complete search history.

(56) References Cited

U.S. PATENT DOCUMENTS

| | | | | |
|---|---|---|---|---|
| 7,863,289 | B2 * | 1/2011 | Spevak et al. ............... | 514/300 |
| 2004/0077595 | A1 | 4/2004 | Cheng et al. | |
| 2008/0167338 | A1 | 7/2008 | Spevak et al. | |
| 2010/0249118 | A1 | 9/2010 | Ibrahim et al. | |

FOREIGN PATENT DOCUMENTS

WO WO-2007/002433 1/2007

OTHER PUBLICATIONS

Bagshawe, Antibody-Directed Enzyme Prodrug Therapy: A Review; 1995, Drug Dev. Res., 34:220-230.
Balak, et. al., Novel D761Y and common secondary T790M mutations in epidermal growth factor receptor-Mutant lung adenocarcinomas with acquired resistance to kinase inhibitors. Clin Cancer Res. (2006), 12:6494-501.
Bertolini et al., A new Rational Hypothesis for the Pharmacophore of the Active Metabolite of Leflunomide, a Potent Immunosuppressive Drug; 1997, J. Med. Chem., 40:2011-2016.
Crump, M., Inhibition of Raf Kinase in the Treatment of Acute Myeloid Leukemia, Curr. Pharm. Design 8(25):2243-8 (2002).
Hood, J.D. et al., Tumor regression by targeted gene delivery to the neovasculature. (2002), Science 296: 2404.
International Search Report and Written Opinion dated Jun. 11, 2010 in related application PCT/US2010/026856.
Kunnimalaiyaan et al., The Raf-1 pathway: a molecular target for treatment of select neuroendocrine tumors? Anticancer Drugs (2006), 17(2):139-42.
Niihori et al., Germline KRAS and BRAF mutations in cardio-facio-cutaneous syndrome. Nat Genet. (2006), 38(3):294-6.
Shan et al., Prodrug Strategies Based on Intramolecular Cyclization Reactions, J Pharm Sci 86(7):765-767 (1997).

* cited by examiner

*Primary Examiner* — Janet Andres
*Assistant Examiner* — Niloofar Rahmani
(74) *Attorney, Agent, or Firm* — Foley & Lardner LLP; Stephen E. Reiter

(57) ABSTRACT

N-[3-(4-Cyano-1H-pyrrolo[2,3-b]pyridine-3-carbonyl)-2,4-difluoro-phenyl]-4-trifluoromethyl-benzenesulfonamide, N-[3-(4-ethynyl-1H-pyrrolo[2,3-b]pyridine-3-carbonyl)-2, 4-difluoro-phenyl]-4-trifluoromethyl-benzenesulfonamide, and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, forms thereof are active on at least one Raf protein kinase. Also described are methods of use thereof to treat diseases and conditions, including diseases and conditions associated with activity of Raf protein kinases, including pain and polycystic kidney disease.

6 Claims, No Drawings

COMPOUNDS AND USES THEREOF

CROSS REFERENCE TO RELATED APPLICATIONS

This application claims priority to U.S. provisional application Ser. Nos. 61/159,401 and 61/159,407 filed Mar. 11, 2009, each of which is incorporated herein in its entirety.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. Also contemplated in accordance with the present invention are methods for the use of compounds in treating diseases and conditions associated with regulation of the activity of one or more Raf kinases, including any mutations of one or more Raf kinases. Thus, in certain embodiments uses are provided for compounds and salt forms thereof in therapeutic methods involving modulation of Raf protein kinases. In one embodiment, compounds or pharmaceutically acceptable salts thereof, are used for therapeutic methods involving modulation of Raf protein kinases, including treatment of a variety of indications, including, but not limited to, pain and polycystic kidney disease.

In a first aspect, a compound selected from the group consisting of N-[3-(4-cyano-1H-pyrrolo[2,3-b]pyridine-3-carbonyl)-2,4-difluoro-phenyl]-4-trifluoromethyl-benzenesulfonamide (P-0001), N-[3-(4-ethynyl-1H-pyrrolo[2,3-b]pyridine-3-carbonyl)-2,4-difluoro-phenyl]-4-trifluoromethyl-benzenesulfonamide (P-0002), any salt thereof, any formulation thereof, any conjugate thereof, any derivative thereof, and any form thereof is provided. In certain embodiments P-0001, P-0002, or a salt thereof, formulation thereof, conjugate thereof, derivative thereof, or form thereof is an inhibitor of one or more Raf protein kinases, including A-Raf, B-Raf, and c-Raf-1 (including any mutations of these kinases).

In a second aspect the compound N-[3-(4-cyano-1H-pyrrolo[2,3-b]pyridine-3-carbonyl)-2,4-difluoro-phenyl]-4-trifluoromethyl-benzenesulfonamide (P-0001), or a salt thereof, formulation thereof, conjugate thereof, derivative thereof, or form thereof is provided. In certain embodiments P-0001, or a salt thereof, formulation thereof, conjugate thereof, derivative thereof, or form thereof is an inhibitor of one or more Raf protein kinases, including A-Raf, B-Raf, and c-Raf-1 (including any mutations of these kinases).

In a third aspect the compound N-[3-(4-ethynyl-1H-pyrrolo[2,3-b]pyridine-3-carbonyl)-2,4-difluoro-phenyl]-4-trifluoromethyl-benzenesulfonamide (P-0002), or a salt thereof, formulation thereof, conjugate thereof, derivative thereof, or form thereof is provided. In certain embodiments P-0002, or a salt thereof, formulation thereof, conjugate thereof, derivative thereof, or form thereof is an inhibitor of one or more Raf protein kinases, including A-Raf, B-Raf, and c-Raf-1 (including any mutations of these kinases).

In reference to compounds P-0001 and P-0002, unless clearly indicated to the contrary, specification of the compound includes salts of such compound (including pharmaceutically acceptable salts), formulations of such compound (including pharmaceutically acceptable formulations), conjugates thereof, derivatives thereof, forms thereof, and prodrugs thereof.

In a fourth aspect, the invention provides methods for treating a Raf protein kinase mediated disease or condition in an animal subject, wherein the method involves administering to the subject an effective amount of either or both of P-0001 or P-0002. In one embodiment, the method involves administering to the subject an effective amount of either or both of P-0001 or P-0002 in combination with one or more other therapies for the disease or condition. In one embodiment, the disease is pain. In one embodiment, the disease is polycystic kidney disease.

In a fifth aspect, compositions are provided that include a therapeutically effective amount of either or both of P-0001 or P-0002 and at least one pharmaceutically acceptable carrier, excipient, and/or diluent. In certain embodiments, the composition can include either or both of P-0001 or P-0002, along with one or more compounds that are therapeutically effective for the same disease indication. In related embodiments, the composition includes either or both of P-0001 or P-0002, along with one or more compounds that are therapeutically effective for the same disease indication, wherein the compounds have a synergistic effect on the disease indication. In one embodiment, the disease is pain. In one embodiment, the disease is polycystic kidney disease.

In a sixth aspect, the invention provides methods for treating a disease or condition mediated by A-Raf, B-Raf, c-Raf-1, or any mutation thereof by administering to the subject an effective amount of a composition including either or both of P-0001 or P-0002. In various embodiments, the invention provides methods for treating a disease or condition mediated by A-Raf, B-Raf, c-Raf-1, or any mutation thereof by administering to the subject an effective amount of a composition including either or both of P-0001 or P-0002 in combination with one or more other suitable therapies for treating the disease. In one embodiment, the disease is pain. In one embodiment, the disease is polycystic kidney disease.

In a seventh aspect, the invention provides kits that include either or both of P-0001 or P-0002, or a composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a protein kinase-mediated disease or condition; and the compound or composition is packaged in unit dose or single dose form, e.g., single dose pills, capsules, or the like.

In aspects and embodiments involving treatment of a disease or condition with either or both of P-0001 or P-0002, the invention provides methods for treating an A-Raf-mediated, B-Raf-mediated and/or c-Raf-1-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). In some embodiments, invention methods may involve administering to the subject suffering from or at risk of an A-Raf-mediated, B-Raf-mediated and/or c-Raf-1-mediated disease or condition an effective amount of either or both of P-0001 or P-0002. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is pain or polycystic kidney disease.

In an eighth aspect, either or both of P-0001 or P-0002, can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is pain or polycystic kidney disease.

Either or both of P-0001 and P-0002, as provided herein, demonstrate desirable inhibitory activity on Raf kinases, with selectivity relative to other kinases, and further demonstrate one or more desirable properties, such as greater solubility, lesser Cyp inhibition, and the like.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

All atoms within P-0001 or P-0002 described herein are intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{11}C$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Raf protein kinase mediated disease or condition" refers to a disease or condition in which the biological function of a Raf protein kinase (also referred to as Raf kinase, or Raf), including any of A-Raf protein kinase, B-Raf protein kinase or c-Raf-1 protein kinase, or any mutation thereof, affects the development, course, and/or symptoms of the disease or condition, and/or in which modulation of Raf alters the development, course, and/or symptoms of the disease or condition. The Raf mediated disease or condition includes a disease or condition for which Raf modulation provides a therapeutic benefit, e.g. wherein treatment with Raf inhibitor(s), including one or more compound(s) described herein, provides a therapeutic benefit to the subject suffering from or at risk of the disease or condition.

As used herein, the term "A-Raf protein kinase mediated disease or condition," and the like refer to a disease or condition in which the biological function of an A-Raf protein kinase (also referred to as A-Raf kinase, or A-Raf), including any mutations thereof, affects the development, course, and/or symptoms of the disease or condition, and/or in which modulation of A-Raf alters the development, course, and/or symptoms of the disease or condition. The A-Raf mediated disease or condition includes a disease or condition for which A-Raf inhibition provides a therapeutic benefit, e.g. wherein treatment with a compound that inhibits A-Raf, including one or more compound(s) described herein, provides a therapeutic benefit to the subject suffering from or at risk of the disease or condition.

As used herein, the term "B-Raf protein kinase mediated disease or condition," and the like refer to a disease or condition in which the biological function of a B-Raf protein kinase (also referred to as B-Raf kinase, or B-Raf), including any mutations thereof, such as B-Raf V600E mutant, or B-Raf V600E/T529I mutant, affects the development, course, and/or symptoms of the disease or condition, and/or in which modulation of B-Raf alters the development, course, and/or symptoms of the disease or condition. The B-Raf mediated disease or condition includes a disease or condition for which B-Raf inhibition provides a therapeutic benefit, e.g. wherein treatment with a compound that inhibits B-Raf, including one or more compound(s) described herein, provides a therapeutic benefit to the subject suffering from or at risk of the disease or condition.

As used herein, the term "B-Raf V600E mutant protein kinase mediated disease or condition," and the like refer to a disease or condition in which the biological function of B-Raf V600E mutant protein kinase (also referred to as B-Raf V600E kinase, or B-Raf V600E) affects the development, course, and/or symptoms of the disease or condition, and/or in which modulation of B-Raf V600E alters the development, course, and/or symptoms of the disease or condition. The B-Raf V600E mediated disease or condition includes a disease or condition for which B-Raf V600E inhibition provides a therapeutic benefit, e.g. wherein treatment with a compound that inhibits B-Raf V600E, including one or more compound(s) described herein, provides a therapeutic benefit to the subject suffering from or at risk of the disease or condition.

As used herein, the term "B-Raf V600E/T529I mutant protein kinase mediated disease or condition," and the like refer to a disease or condition in which the biological function of B-Raf V600E/T529I mutant protein kinase (also referred to as B-Raf V600E/T529I kinase, or B-Raf V600E/T529I) affects the development, course, and/or symptoms of the disease or condition, and/or in which modulation of B-Raf V600E/T529I alters the development, course, and/or symptoms of the disease or condition. The B-Raf V600E/T529I mediated disease or condition includes a disease or condition for which B-Raf V600E/T529I inhibition provides a therapeutic benefit, e.g. wherein treatment with a compound that inhibits B-Raf V600E/T529I, including one or more compound(s) described herein, provides a therapeutic benefit to the subject suffering from or at risk of the disease or condition.

As used herein, the term "c-Raf-1 protein kinase mediated disease or condition," and the like refer to a disease or condition in which the biological function of a c-Raf-1 protein kinase (also referred to as c-Raf-1 kinase, or c-Raf-1), including any mutations thereof, affects the development, course, and/or symptoms of the disease or condition, and/or in which modulation of c-Raf-1 alters the development, course, and/or symptoms of the disease or condition. The c-Raf-1 mediated disease or condition includes a disease or condition for which c-Raf-1 inhibition provides a therapeutic benefit, e.g. wherein treatment with a compound that inhibits c-Raf-1, including one or more compound(s) described herein, provides a therapeutic benefit to the subject suffering from or at risk of the disease or condition.

As used herein, the term "Raf inhibitor" refers to a compound that inhibits at least one of A-Raf, B-Raf, c-Raf-1, or any mutations thereof, i.e. a compound having an $IC_{50}$ of less than 500 nM, less than 100 nM, less than 50 nM, less than 20 nM, less than 10 nM, less than 5 nM, or less than 1 nM as determined in a generally accepted Raf kinase activity assay. Such compounds are preferably, but not necessarily, selective with respect to other protein kinases, i.e. when compared to another protein kinase, the $IC_{50}$ for the other kinase divided by the $IC_{50}$ for the Raf kinase is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of a combination of two or more components, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention follow:

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat. Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

A-Raf, B-Raf and/or c-Raf-1 inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Alternative Compound Forms or Derivatives

Compounds P-0001 or P-0002 contemplated herein are described with reference to the specific compounds. In addition, P-0001 or P-0002 may exist in a number of different forms or derivatives, all within the scope of the present invention. Alternative forms or derivatives, include, for example, (a) prodrugs, and active metabolites (b) tautomers (c) pharmaceutically acceptable salts and (d) solid forms, including different crystal forms, polymorphic or amorphous solids, including hydrates and solvates thereof, and other forms.

(a) Prodrugs and Metabolites

In addition to compounds P-0001 or P-0002 described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. Prodrugs may include variants wherein an —NH group of the compound has undergone acylation, such as the 1-position of the pyrrolo[2,3-b]pyridine ring or the nitrogen of the sulfonamide group of either of P-0001 or P-0002, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers

It is understood that some compounds may exhibit tautomerism. In such cases, the formulae provided herein expressly depict only one of the possible tautomeric forms. It is therefore to be understood that compounds P-0001 or P-0002 provided herein are intended to represent any tautomeric form of the depicted compound and is not to be limited merely to the specific tautomeric form depicted by the drawing of the compound.

(c) Pharmaceutically Acceptable Salts

Unless specified to the contrary, specification of compounds P-0001 or P-0002 herein includes pharmaceutically acceptable salts of such compound. Thus, compounds P-0001 or P-0002 can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Compounds P-0001 or P-0002 possess a sufficiently acidic and a sufficiently basic functional group, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, either of compounds P-0001 or P-0002 is complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining either of compounds P-0001 or P-0002 with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, either of compounds P-0001 or P-0002 are intended to cover hydrated or solvated as well as unhydrated or unsolvated forms of the identified material. For example, either of compounds P-0001 or P-0002 or salts thereof includes both hydrated and non-hydrated forms. Other examples of solvates include either of compounds P-0001 or P-0002 in combination with a suitable solvent, such as isopropanol, ethanol, methanol, DMSO, ethyl acetate, acetic acid, or ethanolamine.

Formulations and Administration

Either of compounds P-0001 or P-0002 or any form thereof as described herein will typically be used in therapy for human subjects. However, either of compounds P-0001 or P-0002 and compositions thereof may also be used to treat similar or identical indications in other animal subjects, and can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Either of compounds P-0001 or P-0002 may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as cross-linked polyvinylpyrrolidone, agar, or alginic acid, or a salt thereof such as sodium alginate; a lubricant, such as talc or magnesium stearate; a plasticizer, such as glycerol or sorbitol; a sweetening agent such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compound may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Either of compounds P-0001 or P-0002 and compositions thereof for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, either of compounds P-0001 or P-0002 or compositions thereof may be formulated in solid form, including, for example, lyophilized forms, and redissolved or suspended prior to use.

In some embodiments, transmucosal, topical or transdermal administration may be used. In such formulations of either of compounds P-0001 or P-0002, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of either of compounds P-0001 or P-0002 for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, either of compounds P-0001 or P-0002 or compositions thereof are administered as inhalants. Either of compounds P-0001 or P-0002 or compositions thereof may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. Either of compounds P-0001 or P-0002 or compositions thereof may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of either of compounds P-0001 or P-0002 or compositions thereof to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

Either of compounds P-0001 or P-0002 or compositions thereof may also be used in combination with other therapies for treating the same disease. Such combination use includes administration of either of compounds P-0001 or P-0002 and one or more other therapeutics at different times, or co-administration of either of compounds P-0001 or P-0002 and one or more other therapies. In some embodiments, dosage may be modified for either of compounds P-0001 or P-0002 or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than either of compounds P-0001 or P-0002 or compositions thereof, or at the same time as either of compounds P-0001 or P-0002 or compositions thereof. Use in combination also includes use with a therapy or medical procedure that is administered once or infrequently, such as surgery, along with either of compounds P-0001 or P-0002 or compositions thereof administered within a short time or longer time before or after the other therapy or procedure. In some embodiments, the present invention provides for delivery of either of compounds P-0001 or P-0002 or compositions thereof and one or more other drug therapeutics delivered by a different route of administration or by the same route of administration. The use in combination for any route of administration includes delivery of either of compounds P-0001 or P-0002 or compositions thereof and one or more other drug therapeutics delivered by the same route of administration together in any formulation, including formulations where the two compounds are chemically linked in such a way that they maintain their therapeutic activity when administered. In one aspect, the other drug therapy may be co-administered with either of compounds P-0001 or P-0002 or compositions thereof. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of either of compounds P-0001 or P-0002 and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent. Synthesis of known compounds for formation of solid forms can be found, for example, in U.S. patent application Ser. No. 11/473,347 (see also, PCT publication WO2007002433), and U.S. patent application Ser. No. 11/960,590 (Publication number 2008/0167338), the disclosures of which are hereby incorporated by reference regarding methods of making compounds.

Example 1

Synthesis of N-[3-(4-cyano-1H-pyrrolo[2,3-b]pyridine-3-carbonyl)-2,4-difluoro-phenyl]-4-trifluoromethyl-benzenesulfonamide P-0001

N-[3-(4-Cyano-1H-pyrrolo[2,3-b]pyridine-3-carbonyl)-2,4-difluoro-phenyl]-4-trifluoromethyl-benzenesulfonamide P-0001 was synthesized in four steps from 2,4-difluoro-phenylamine 1 as shown in Scheme 1.

Scheme 1

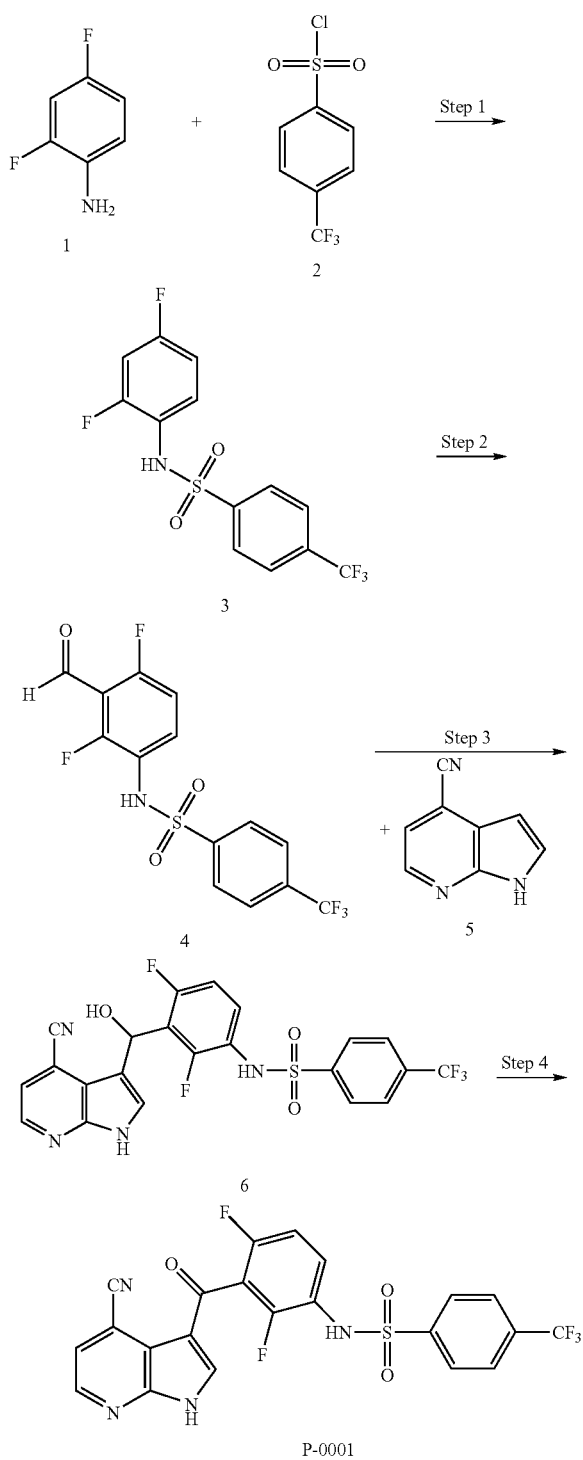

Step 1—Preparation of N-(2,4-difluoro-phenyl)-4-trifluoromethyl-benzenesulfonamide (3)

To 2,4-difluoro-phenylamine (1, 2.09 mL, 20.7 mmol) in 13.04 mL of dichloromethane, pyridine (0.522 mL, 6.45 mmol) was added and the mixture was stirred under nitrogen for 20 minutes. 4-Trifluoromethyl-benzenesulfonyl chloride (2, 5.00 g, 20.4 mmol) was added slowly and the reaction was stirred overnight. The reaction mixture was treated with 2 mL of 1 M hydrochloric acid in diethyl ether and allowed to sit for 1 hour. The solid precipitate was filtered off, and the filtrate was extracted with 1 N aqueous hydrochloric acid followed by brine. The organic portion was dried over magnesium sulfate, filtered and the filtrate was concentrated under vacuum. The resulting solid was treated with dichloromethane, and the solid was collected and dried to provide the desired compound as a white solid (3, 2.383 g).

Step 2—Preparation of N-(2,4-difluoro-3-formyl-phenyl)-4-trifluoromethyl-benzenesulfonamide (4)

Into a round bottom flask containing N,N-diisopropylamine (2.692 mL, 19.21 mmol) in 50.0 mL or tetrahydrofuran, n-butyllithium (2.50 M in hexane, 7.684 mL, 19.21 mmol) was added at −78° C. under an atmosphere of nitrogen. After stirring at −78° C. for 30 minutes, N-(2,4-difluoro-phenyl)-4-trifluoromethyl-benzenesulfonamide (3, 2.09 g, 6.20 mmol) was added, with continued stirring at −78° C. under nitrogen for one hour. The reaction was allowed to come to room temperature over 15 minutes, then poured into water, acidified with 1 N aqueous hydrochloric acid to pH=1, and extracted with ethyl acetate. The organic layers were combined and washed with brine, then dried over sodium sulfate, filtered and the filtrate concentrated under vacuum. The resulting material was purified by silica gel column chromatography, the appropriate fractions were combined, and the solvents removed to provide the desired compound (4, 1.02 g). MS (ESI) [M−H$^+$]$^-$=364.1.

Step 3—Preparation of N-{3-[(4-Cyano-1H-pyrrolo[2,3-b]pyridin-3-yl)-hydroxy-methyl]-2,4-difluoro-phenyl}-4-trifluoromethyl-benzenesulfonamide (6)

Into a round bottom flask 1H-pyrrolo[2,3-b]pyridine-4-carbonitrile (5, 0.054 g, 0.38 mmol), N-(2,4-difluoro-3-formyl-phenyl)-4-trifluoromethyl-benzenesulfonamide (4, 0.179 g, 0.49 mmol), 0.75 mL of methanol and potassium hydroxide (0.103 g, 1.89 mmol) were combined. The reaction was stirred at room temperature for 46 hours, then neutralized with 0.1 N aqueous hydrochloric acid and extracted 3× with ethyl acetate. The organic layers were combined and washed with brine, then dried over sodium sulfate, filtered and the filtrate concentrated under vacuum. The material was purified by silica gel column chromatography eluting with ethyl acetate and hexane. The appropriate fractions were combined and the solvent removed under vacuum to provide the desired compound (6, 0.018 g). MS (ESI) [M+H$^+$]$^+$=509.1.

Step 4—Preparation of N-[3-(4-cyano-1H-pyrrolo[2,3-b]pyridine-3-carbonyl)-2,4-difluoro-phenyl]-4-trifluoromethyl-benzenesulfonamide (P-0001)

To N-{3-[(4-cyano-1H-pyrrolo[2,3-b]pyridin-3-yl)-hydroxy-methyl]-2,4-difluoro-phenyl}-4-trifluoromethyl-benzenesulfonamide (6, 15 mg, 0.030 mmol) dissolved in 0.2 mL of tetrahydrofuran, Dess-Martin periodinane (13.8 mg, 0.0324 mmol) was added. The reaction mixture was stirred at room temperature for one hour. The reaction mixture was poured into saturated sodium thiosulfate, the organic layer separated and washed with brine, then dried over sodium sulfate and filtered. The filtrate was concentrated under vacuum and the resulting material was purified by silica gel column chromatography, eluting with ethyl acetate and hexane. The appropriate fractions were combined and the solvent removed under vacuum to provide the desired compound (P-0001, 4 mg). MS (ESI) [M−H⁺]⁻=505.5.

Example 2

Synthesis of N-[3-(4-ethynyl-1H-pyrrolo[2,3-b]pyridine-3-carbonyl)-2,4-difluoro-phenyl]-4-trifluoromethyl-benzenesulfonamide P-0002

N-[3-(4-ethynyl-1H-pyrrolo[2,3-b]pyridine-3-carbonyl)-2,4-difluoro-phenyl]-4-trifluoromethyl-benzenesulfonamide P-0002 was synthesized in four steps from 2,4-difluoro-phenylamine 1 as shown in Scheme 2.

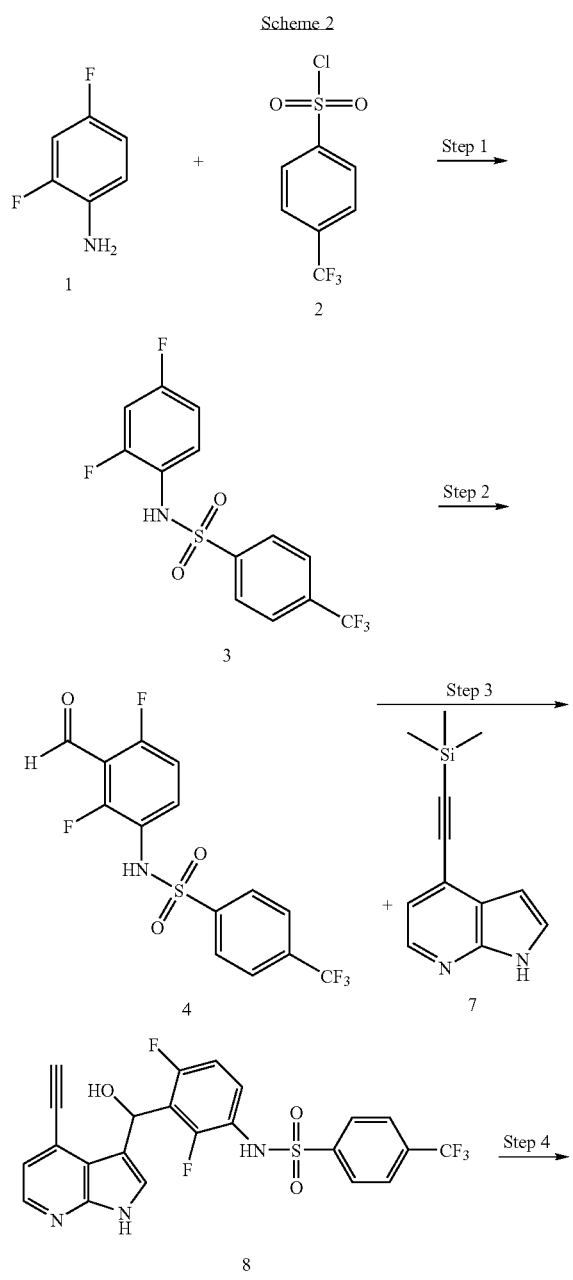

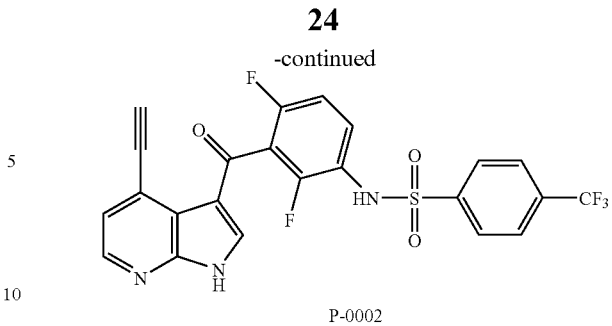

Step 1—Preparation of N-(2,4-difluoro-phenyl)-4-trifluoromethyl-benzenesulfonamide (3)

Per Scheme 1.

Step 2—Preparation of N-(2,4-difluoro-3-formyl-phenyl)-4-trifluoromethyl-benzenesulfonamide (4)

Per Scheme 1.

Step 3—Preparation of N-{3-[(4-Ethynyl-1H-pyrrolo[2,3-b]pyridin-3-yl)-hydroxy-methyl]-2,4-difluoro-phenyl}-4-trifluoromethyl-benzenesulfonamide (8)

Into a round bottom flask 4-trimethylsilanylethynyl-1H-pyrrolo[2,3-b]pyridine (7, 0.250 g, 1.17 mmol), N-(2,4-difluoro-3-formyl-phenyl)-4-trifluoromethyl-benzenesulfonamide (4, 0.498 g, 1.36 mmol), and 2.0 mL of methanol were added and the suspension was stirred for 10 minutes. Potassium hydroxide (0.213 g, 3.79 mmol) was added and the reaction was stirred at room temperature for 6 hours. The reaction was poured into 25 mL of water and 25 mL of saturated ammonium chloride, then extracted with 50 mL or ethyl acetate. The organic layer was isolated and concentrated under vacuum. The residue was purified by silica gel column chromatography, eluting with a gradient of 5 to 60% ethyl acetate in hexanes. The appropriate fractions were combined and the solvents removed under vacuum to provide the desired compound (8, 0.146 g).

Step 4—Preparation of N-[3-(4-ethynyl-1H-pyrrolo[2,3-b]pyridine-3-carbonyl)-2,4-difluoro-phenyl]-4-trifluoromethyl-benzenesulfonamide (P-0002)

To N-{3-[(4-ethynyl-1H-pyrrolo[2,3-b]pyridin-3-yl)-hydroxy-methyl]-2,4-difluoro-phenyl}-4-trifluoromethyl-benzenesulfonamide (8, 0.146 g, 0.288 mmol) dissolved in 15 mL of tetrahydrofuran, Dess-Martin periodinane (0.122 g, 0.288 mmol) was added. The reaction mixture was stirred at room temperature for 15 minutes. The reaction mixture was poured into water, extracted with ethyl acetate, and the organic layer separated and washed with brine, then dried over magnesium sulfate and filtered. The filtrate was concentrated under vacuum and the resulting material was purified by silica gel column chromatography, eluting with 0 to 30% ethyl acetate and hexane. The appropriate fractions were combined and the solvent removed under vacuum, and this material was further purified by silica gel column chromatography, eluting with 0 to 15% ethyl acetate and hexane. The appropriate fractions were combined and the solvent removed under vacuum to provide the desired compound (P-0001, 121 mg). MS (ESI) [M+H⁺]⁺=506.

Example 3

Salt Forms of Compounds P-0001 or P-0002

P-0001 or P-0002 are characterized as having functionalities providing both weakly basic and weakly acidic centers which can form organic salt complexes, resulting in improved solubility. For example, the N-7 of the pyrrolo[2,3-b]pyridine portion is weakly basic (pKa approximately 4-5) while the sulfonamide nitrogen is weakly acidic (pKa approximately 7). Due to the weakly basic and weakly acidic centers, salts or salt complexes may be prepared by either acid addition or base addition.

Base addition salts, preferably organic base addition salts, including ammonium, diethylamine, ethanolamine, ethylenediamine, diethanolamine, t-butylamine, piperazine, meglumine, L-arginine, L-histidine, and L-lysine are formed by dissolving P-0001 or P-0002 in 20-50 solvent volumes of an alcohol (such as methanol, ethanol, isopropanol) or other suitable solvent, such as acetone, with moderate heating (30-35° C.). The suspension is stirred, and 1 equivalent of the base that has been triturated in a separate portion of the solvent is added. The mixture is stirred under an inert atmosphere until a clear solution is formed. The solution is filtered and the solvent removed from the filtrate under reduced pressure. The resulting film forms a friable solid upon vacuum drying. Alternatively, the salt form is precipitated by addition of cold solvent such as heptane, methyl t-butyl ether, ethyl acetate or the like to the solution, the resulting solid filtered and vacuum dried to isolate the friable solid. The resulting solid is assessed for physical properties including DSC, XRPD, solubility and intrinsic dissolution.

Acid addition salts, preferably organic acid addition salts, including acetate, besylate, camsylate, formate, fumarate, maleate, mesylate, nitrate, oxalate, tartrate, thiocyanate, and tosylate are formed by adding P-0001 or P-0002 to 20-50 solvent volumes of acetone (or other suitable solvent) with stirring and heating (30-35° C.), followed by the addition of 1 equivalent of the acid. The solution is slowly cooled to 2-8° C. and the solid is isolated by either filtration or centrifugation, followed by vacuum drying. The resulting solid is assessed for physical properties including DSC, XRPD, solubility and intrinsic dissolution.

Additional organic acid salts or salt complexes, including citric acid, tartaric acid, succinic acid, glutaric acid and acetylsalicylic acid salts or salt complexes of P-0001 or P-0002 are formed in 1:1 or 1:2 compound:acid ratios in a suitable solvent such as methanol. P-0001 or P-0002 is added to 15-20 solvent volumes of methanol, with the desired solid isolated by either spray drying or by addition of non-solvent such as heptane followed by filtration and vacuum drying. The resulting solid is assessed for physical properties including DSC, XRPD, solubility and intrinsic dissolution.

Mineral acids, including sulfate, phosphate and hydrochloric acid salts of P-0001 or P-0002 are prepared from methanol or ethyl acetate solutions.

The resulting salts or salt complexes may also be processed to provide a preferred amorphous form, such as through spray-drying techniques or microprecipitated bulk processing, or may be processed with suitable excipient materials to provide for a directly compressible or encapsulated dosage form. Salts or salt complexes may also be achieved by mechanochemical (e.g. roller compaction) or microwave irradiation of the parent compound with the appropriate selection of charge transfer partner. Such an approach is used to minimize solvent utilization, increase yield, purity and throughput, as well as achieve constructs not attainable using conventional solvent techniques.

Example 4

Compound Properties

While the inhibitory activity of P-0001 or P-0002 on any Raf kinase is important to their activity in treating disease, the compounds described herein show favorable properties that provide advantages as a pharmaceutical as well. In addition to demonstrating kinase inhibitory activity against Raf kinases in biochemical assays, compounds may show favorable solubility, favorable pharmacokinetic properties, and low Cyp inhibition. The compounds are assessed in the following assays or similar assays available to one skilled in the art.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of B-Raf kinase activity, c-Raf-1 kinase activity, or B-Raf V600E kinase activity, where inhibition of phosphorylation of a peptide substrate is measured as a function of compound concentration. Compounds to be tested are diluted in dimethyl sulfoxide to a concentration of 0.1 mM. These are serially diluted 15 µL into 30 µL of dimethyl sulfoxide seven times in 96 well plates for a total of 8 dilution points, and for each dilution point 1 µL is added to a well of an assay plate. Plates are prepared such that each well in a 384 well plate contains 1 µL of compound in 10 µL volume with 0.1 ng Raf enzyme (i.e. any of B-Raf, c-Raf-1 or B-Raf V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 µL of 200 µM ATP (i.e. final 100 µM ATP). After incubation of the kinase reaction for 45 minutes at room temperature, 5 µL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti phosphor MEK1/2 antibody (CellSignal), each at final concentration 10 µg/mL). The plates are incubated for 3 hours at room temperature and read on Envision reader (Perkin Elmer). Phosphorylation of Mek1 results in binding of the anti-phosphor-MEK1/2 antibody and association of the donor and acceptor beads such that signal correlates with kinase activity. The signal vs. compound concentration is used to determine the $IC_{50}$.

The inhibitory activity of P-0001 or P-0002 against Raf kinases as well as other kinases in a biochemical assay shows selective activity to the Raf kinases. The data show $IC_{50}$ of <0.1 µM for B-Raf and c-Raf-1, and <1 µM for B-Raf mutant V600E for both compounds, while for P-0001 activity for Kit, TrkA and Src was between 1-10 µM, and Btk, Fms, Hgk, and Kdr was greater than 10 µM and for P-0002 activity for Kdr and Src was ~1 µM, and Btk, Fms, and TrkA was greater than 10 µM.

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer is added to each well, and 1 μL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 μM, moderate solubility if the threshold concentration is 31.3 μM to 250 μM, and high solubility if the threshold concentration is >250 μM.

The following table provides data indicating the relative solubility (L=low, M=moderate, H=high) based on turbidity threshold concentration at each pH for P-0001 and P-0002:

| Compound | turbidity threshold (L, M, H) | | | |
|---|---|---|---|---|
| number | 1.4 | 4.5 | 6.8 | 7.4 |
| P-0001 | L | L | L | M |
| P-0002 | L | L | M | M |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in dimethyl sulfoxide to a concentration of 100 mM. These are diluted 1 μL into 82 μL of acetonitrile. An 11 μL aliquot of this solution is then added to 204 μL of cofactor mix (1.3% NADPH Regeneration system Solution A, 1.04% NADPH Regeneration system Solution B from BD Biosciences, 5% acetonitrile and 0.05% dimethyl sulfoxide). These are then serially diluted 160 μL to 160 μL co-factor mix for a total of 10 points. A 10 μL aliquot of this final mixture is dispensed into 384 well assay plates and incubated for 10 minutes at 37° C. Enzyme and substrate mix (10 μL; 0.5 pmol CYP1A2/5 μM CEC; 1.0 pmol CYP2C9/75 μM MFC; 0.5 pmol CYP2C19/25 μM CEC; 1.5 pmol CYP2D6/1.5 μM AMMC; 1.0 pmol CYP3A4/50 μM BFC; or 1.0 pmol CYP3A4/40 μM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 μM, more preferably $IC_{50}$ values of >10 μM.

The following table provides data indicating the Cyp inhibitory activity for P-0001 and P-0002:

| Compound | Cyp $IC_{50}$ (μM) | | | | | |
|---|---|---|---|---|---|---|
| number | 1A2 | 2C19 | 2C9 | 2D6 | 3A4(BFC) | 3A4(BQ) |
| P-0001 | >10 | >10 | >10 | >10 | >10 | >10 |
| P-0002 | >10 | >10 | <5 | >10 | 5-10 | >10 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound selected from the group consisting of N-[3-(4-cyano-1H-pyrrolo[2,3-b]pyridine-3-carbonyl)-2,4-difluoro-phenyl]-4-trifluoromethyl-benzenesulfonamide, N-[3-(4-ethynyl-1H-pyrrolo[2,3-b]pyridine-3-carbonyl)-2,4-difluoro-phenyl]-4-trifluoromethyl-benzenesulfonamide and a pharmaceutically acceptable salt thereof.

2. The compound according to claim 1 that is N-[3-(4-cyano-1H-pyrrolo[2,3-b]pyridine-3-carbonyl)-2,4-difluoro-phenyl]-4-trifluoromethyl-benzenesulfonamide, or a pharmaceutically acceptable salt thereof.

3. The compound according to claim 1 that is N-[3-(4-ethynyl-1H-pyrrolo[2,3-b]pyridine-3-carbonyl)-2,4-difluoro-phenyl]-4-trifluoromethyl-benzenesulfonamide, or a pharmaceutically acceptable salt thereof.

4. A composition comprising the compound or salt thereof according to claim 1 and one or more pharmaceutically acceptable excipients.

5. A kit comprising the compound or salt thereof according to claim 1.

6. A kit comprising the composition according to claim 4.

* * * * *